US011023046B2

(12) United States Patent
Ketz et al.

(10) Patent No.: US 11,023,046 B2
(45) Date of Patent: Jun. 1, 2021

(54) SYSTEM AND METHOD FOR CONTINUAL DECODING OF BRAIN STATES TO MULTI-DEGREE-OF-FREEDOM CONTROL SIGNALS IN HANDS FREE DEVICES

(71) Applicant: HRL LABORATORIES, LLC, Malibu, CA (US)

(72) Inventors: Nicholas A. Ketz, Madison, WI (US); Aashish Patel, Malibu, CA (US); Michael D. Howard, Westlake Village, CA (US); Praveen K. Pilly, Tarzana, CA (US); Jaehoon Choe, Agoura Hills, CA (US)

(73) Assignee: HRL Laboratories, LLC, Malibu, CA (US)

( * ) Notice: Subject to any disclaimer, the term of this patent is extended or adjusted under 35 U.S.C. 154(b) by 0 days.

(21) Appl. No.: 16/890,406

(22) Filed: Jun. 2, 2020

(65) Prior Publication Data

US 2021/0004085 A1 Jan. 7, 2021

Related U.S. Application Data

(60) Provisional application No. 62/869,867, filed on Jul. 2, 2019.

(51) Int. Cl.
*G06F 3/01* (2006.01)
*G06N 3/08* (2006.01)
*A61B 5/375* (2021.01)

(52) U.S. Cl.
CPC .............. *G06F 3/015* (2013.01); *A61B 5/375* (2021.01); *G06N 3/08* (2013.01)

(58) Field of Classification Search
None
See application file for complete search history.

(56) References Cited

U.S. PATENT DOCUMENTS 9,050,200 B2 6/2015 Digiovanna et al.
2010/0137734 A1* 6/2010 Digiovanna ......... A61B 5/0482
600/545

(Continued)

FOREIGN PATENT DOCUMENTS

KR 1020190030612 A 3/2019
WO WO2018141061 A1 8/2018

OTHER PUBLICATIONS

Prins et al. A confidence metric for using neurobiological feedback in actor-critic reinforcement learning based brain-machine interfaces, frontiers in Neuroscience. May 2014, vol. 8, Article 111. (Year: 2014).*

(Continued)

*Primary Examiner* — Etsub D Berhanu
(74) *Attorney, Agent, or Firm* — Lewis Roca Rothgerber Christie, LLP (57) ABSTRACT

A brain-machine interface system configured to decode neural signals to control a target device includes a sensor to sample the neural signals, and a computer-readable storage medium having software instructions, which, when executed by a processor, cause the processor to transform the neural signals into a common representational space stored in the system, provide the common representational space as a state representation to inform an Actor recurrent neural network policy of the system, generate and evaluate, utilizing a deep recurrent neural network of the system having a generative sequence decoder, predictive sequences of control signals, supply a control signal to the target device to achieve an output of the target device, determine an intrinsic biometric-based reward signal, from the common representational space, based on an expectation of the output of the target device, and supply the intrinsic biometric-based reward signal to a Critic model of the system.

20 Claims, 5 Drawing Sheets
(2 of 5 Drawing Sheet(s) Filed in Color)

(56) References Cited

U.S. PATENT DOCUMENTS

| | | |
|---|---|---|
| 2017/0364829 A1 | 12/2017 | Fyffe |
| 2019/0025917 A1 | 1/2019 | Francis et al. |
| 2019/0101985 A1* | 4/2019 | Sajda ............ G06F 3/017 |

OTHER PUBLICATIONS

Prins et al. Feedback for reinforcement learning based brain-machine interfaces using confidence metrics. Journal of Neural Engineering. 14 (2017). (Year: 2017).*

Matsumoto et al. Design of a brain computer using the novel principles of output-driven operation and memory-based architecture. International Congress Series 1250 (2003) 529-546. (Year: 2003).*

Mnih et al. Asynchronous Methods for Deep Reinforcement Learning. 2016. (Year: 2016).*

Iturrate et al. Robot Reinforcement Learning using EEG-based reward signals. (Year: 2010).*

Spuler et al. Online Adaptation of a c-VEP Brain-Computer Interface(BCI) Based on Error-Related Potentials and Unsupervised Learning. PLOS ONE. 2012. (Year: 2012).*

Prins et al. Feature Extraction and Unsupervised Classification of Neural Population Reward Signals for Reinforcement Based BMI. 35th Annual International Conference of the IEEE EMBS, 2013. (Year: 2013).*

Pohlmeyer et al. Brain-Machine Interface Control of a Robot Arm using Actor-Critic Reinforcement Learning. 34th Annual International Conference of the IEEE EMBS, 2012. (Year: 2012).*

Yoon et al. Adaptive classification for Brain Computer Interface systems using Sequential Monte Carlo sampling. Neural Networks 22 (2009) 1286-1294. (Year: 2009).*

Sussillo et al. A recurrent neural network for closed-loop intracortical brain-machine interface decoders. Journal of Neural Engineering, 9 (2012). (Year: 2012).*

Sussillo et al. Making brain-machine interfaces robust to future neural variability. Nature Communications, 2016. (Year: 2016).*

Huh et al. Real-Time Motor Control using Recurrent Neural Networks, 2009. (Year: 2009).*

Tuan et al. Improving Conditional Sequence Generative Adversarial Networks by Stepwise Evaluation. (Year: 2019).*

Collins et al., "Ownership of an artificial limb induced by electrical brain stimulation," PNAS, 114(1): 166-171, 2017.

Dmochowski et al., "Optimized multi-electrode stimulation increases focality and intensity at target," Journal of Neural Engineering, 16 pages, 2011.

Gharabaghi, "Coupling brain-machine interfaces with cortical stimulation for brain-state dependent stimulation enhancing motor cortex excitability for neurorehabilitation," Frontiers in Human Neuroscience, vol. 8, Article 122, 7 pages, 2014.

Holdefer et al., "Predicted current densities in the brain during transcranial electrical stimulation," Clin Neurophysical, 117(6): 1388-1397, Jun. 2006.

Lee et al., "Image-Guided Transcranial Focused Ultrasound Stimulates Human Primary Somatosensory Cortex," Scientific Reports, 10 pages, 2015.

Lee et al., "Transcranial focused ultrasound stimulation of human primary visual cortex," Scientific Reports, 12 pages, 2016.

Muller et al., "Cortical travelling waves: mechanisms and computational principles," Nat Rev Neurosci., 19(5): 255-268, May 2018.

Stepp et al., "Relative to direct haptic feedback, remote vibrotactile feedback improves but slows object manipulation," IEEE EMBS, 4 pages, 2010.

Tan et al., "Decoding gripping force based on local field potentials recorded from subthalamic nucleus in humans," eLIFE, 24 pages, 2016.

Tiran et al., "Transcranial Functional Ultrasound Imaging in Freely Moving Awake Mice and Anesthetized Young Rats Without Contrast Agent," Ultrasound in Medicine and Biology, 43(8): 1679-1689, 2017.

Feilong et al., "Reliable individual differences in fine-grained cortical functional architecture," NeuroImage, 183: 375-386, 2018.

Herrmann, "Human EEG responses to 1-100 Hz flicker: resonance phenomena in visual cortex and their potential correlation to cognitive phenomena," Exp Brain Res 137: 346-353, 2001.

Mathan et al., "Rapid image analysis using neural signals," 6 pages, 2008.

Pohlmeyer et al., "Using Reinforcement Learning to Provide Stable Brain-Machine Interface Control Despite Neural Input Reorganization," PLOS ONE, 9(1): e87253-12, 2014.

Van Uden et al., "Modeling Semantic Encoding in a Common Neural Representational Space," Frontiers in Neuroscience, vol. 12, Article 437, 14 pages, 2018.

Yu et al., "SeqGAN: Sequence Generative Adversarial Nets with Policy Gradient," arXiv:1609.05473v6, 11 pages, 2017.

Zhao et al., "Paradigm Shift in Sensorimotor Control Research and Brain Machine Interface Control: The Influence of Context on Sensorimotor Representations," Frontiers in Neuroscience, vol. 12, Article 579, 15 pages, 2018.

International Search Report dated Sep. 11, 2020, issued in corresponding International Application No. PCT/US2020/035724, 3 pages.

Written Opinion of the International Searching Authority dated Sep. 11, 2020, issued in corresponding International Application No. PCT/US2020/035724, 4 pages.

* cited by examiner

SYSTEM AND METHOD FOR CONTINUAL DECODING OF BRAIN STATES TO MULTI-DEGREE-OF-FREEDOM CONTROL SIGNALS IN HANDS FREE DEVICES

CROSS-REFERENCE TO RELATED APPLICATION(S)

The present application claims priority to and the benefit of U.S. Provisional Application No. 62/869,867, filed Jul. 2, 2019, the entire contents of which are incorporated herein by reference.

BACKGROUND

1. Field

The present disclosure relates generally to systems and methods for decoding neural signals into control signals for target devices.

2. Description of Related Art

Brain-Machine Interface (BMI) systems may be utilized to decode a user's neural signals into control signals. In some related art BMI systems that do not explicitly follow a stereotypical stimulus-response paradigm, decoders utilize the endogenous "event related potential" (ERP) of the user's brain as the control signal. ERP are involuntary electrical brain signals that can be detected transcranially, usually in a 300-millisecond or 400-millisecond window of time, and are typically limited to a single binary signal. In these scenarios, the control signal capacity increases but at the cost of lower accuracy. A more general electroencephalogram (EEG) BMI is known as biofeedback, where the user learns to control some aspect of EEG, such as the level of alpha waves. Typically, an external computer produces an auditory or visual indication of the EEG aspect the user wants to learn to control, and that indication helps the user to learn the appropriate brain state. Subsequently, it would be possible for the user to control some aspect of a machine or device by producing that brain state. However, in this related art system, the control signal has one degree of freedom, has super high latency, is very inaccurate, and completely dependent on the user learning.

SUMMARY

The present disclosure relates to various embodiments of a brain-machine interface system configured to decode neural signals to control a target device. In one embodiment, the brain-machine interface system includes at least one sensor configured to sample the neural signals, and a computer-readable storage medium having software instructions stored therein, which, when executed by a processor, cause the processor to transform the neural signals into a common representational space stored in the brain-machine interface system, provide the common representational space as a state representation to inform an Actor recurrent neural network policy of the brain-machine interface system, generate and evaluate, utilizing a deep recurrent neural network of the brain-machine interface system having a generative sequence decoder, predictive sequences of control signals for the target device, supply a specific control signal derived from the predictive sequences of control signals to the target device to achieve an output of the target device, determine an intrinsic biometric-based reward signal, from the common representational space, based on an expectation of the output of the target device, and supply the intrinsic biometric-based reward signal to a Critic model of the brain-machine interface system.

The at least one sensor may be configured to sample the neural signals invasively or non-invasively.

The at least one sensor may include an invasive electrocorticographic (ECoG) device or an intracranial electroencephalography (iEEG) device.

Transforming the neural signals into the common representational space may include identifying regions of the neural signals with informative activations for controlling the target device, and performing subject-specific transforms to align the regions across different users.

The intrinsic biometric-based reward may be a positive emotional response when the output of the target device matches a user's intended output.

The intrinsic biometric-based reward may be a negative emotional response when the output of the target device does not match a user's intended output.

The software instructions, when executed by the processor, may cause the processor to generate and evaluate the predictive sequences of the control signals utilizing a tree search.

The present disclosure is also directed to various embodiments of a non-transitory computer-readable storage medium. In one embodiment, the non-transitory computer-readable storage medium has software instructions stored therein, which, when executed by a processor, cause the processor to transform neural data from an individual user into a common representational space of a brain-machine interface system, provide the common representational space as a state representation to inform an Actor recurrent neural network policy of the brain-machine interface system, generate and evaluate, utilizing a deep recurrent neural network of the brain-machine interface system having a generative sequence decoder, predictive sequences of control signals for a target device, supply a specific control signal derived from the predictive sequences of control signals to the target device to produce an output of the target device, determine an intrinsic biometric-based reward, from the common representational space, based on the individual user's expectation of the output of the target device, and supply the intrinsic biometric-based reward to a Critic model of the brain-machine interface system.

The instructions, when executed by a processor, may cause the processor to transform the neural data into the common representational space by identifying regions of the neural data with informative activations for controlling the target device, and performing subject-specific transforms to align the regions across different users.

The instructions, when executed by a processor, may cause the processor to determine the intrinsic biometric-based reward by decoding an emotional response from the individual user to the output of the target device.

The intrinsic biometric-based reward may be a positive emotional response when the output of the target device matches the individual user's intended output.

The intrinsic biometric-based reward may be a negative emotional response when the output of the target device does not match the individual user's intended output.

The software instructions, when executed by the processor, may cause the processor to generate and evaluate the predictive sequences of the control signals utilizing a tree search.

The present disclosure is also directed to various methods of controlling a target device utilizing neural data. In one embodiment, the method includes sampling the neural data from a user, transforming the neural data into a common representational space of a brain-machine interface system, supplying the common representational space as a state representation to inform an Actor recurrent neural network policy of the brain-machine interface system, generating and evaluating, utilizing a deep recurrent neural network of the brain-machine interface system having a generative sequence decoder, predictive sequences of control signals for the target device, supplying a specific control signal derived from the predictive sequences of control signals to the target device to produce an output of the target device, determining an intrinsic reward, from the common representational space, based on the user's expectation of the output of the target device, and supplying the intrinsic reward to a Critic model of the brain-machine interface system.

Evaluating the predictive sequences of the control signals may include a tree search.

Transforming the neural data into the common representational space may include identifying regions of the neural data with informative activations for controlling the target device, and performing subject-specific transforms to align the regions across different users.

Determining the intrinsic reward may include decoding an emotional response from the user to the output of the target device.

The emotional response may be a positive emotional response when the output of the target device is expected.

The emotional response may be a negative emotional response when the output of the target device is unexpected.

Sampling the neural data from the user is performed invasively or non-invasively.

This summary is provided to introduce a selection of concepts that are further described below in the detailed description. This summary is not intended to identify key or essential features of the claimed subject matter, nor is it intended to be used in limiting the scope of the claimed subject matter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The features and advantages of embodiments of the present disclosure will be better understood by reference to the following detailed description when considered in conjunction with the accompanying figures. In the figures, like reference numerals are used throughout the figures to reference like features and components. The figures are not necessarily drawn to scale.

DETAILED DESCRIPTION

The present disclosure is directed to various embodiments of brain-machine interface (BMI) systems and methods for determining control signals for controlling the movements of an external hands-free device, such as a six degree-of-freedom (DOF) robot, from sensed dynamic properties of the brain of a user (e.g., blood flow or electrical emanations of the user's brain). These control signals may be, for instance, steering commands to an unmanned aerial vehicle or control signals to a robot arm. According to various embodiments of the present disclosure, the neural signals of the user may be sensed invasively (e.g., from sensors surgically implanted inside the brain) or non-invasively (e.g., by sensors placed outside the user's skull).

Figure 1:
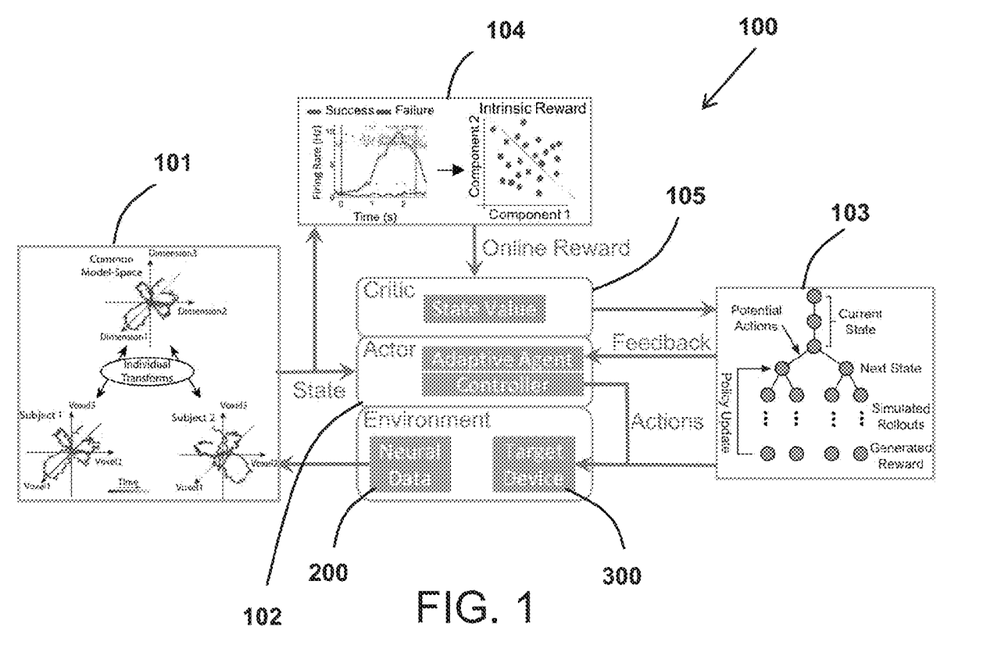
FIG. 1 is a brain-machine interface (BMI) system for decoding neural signals into control signals for a target device according to one embodiment of the present disclosure.
Figure 2:
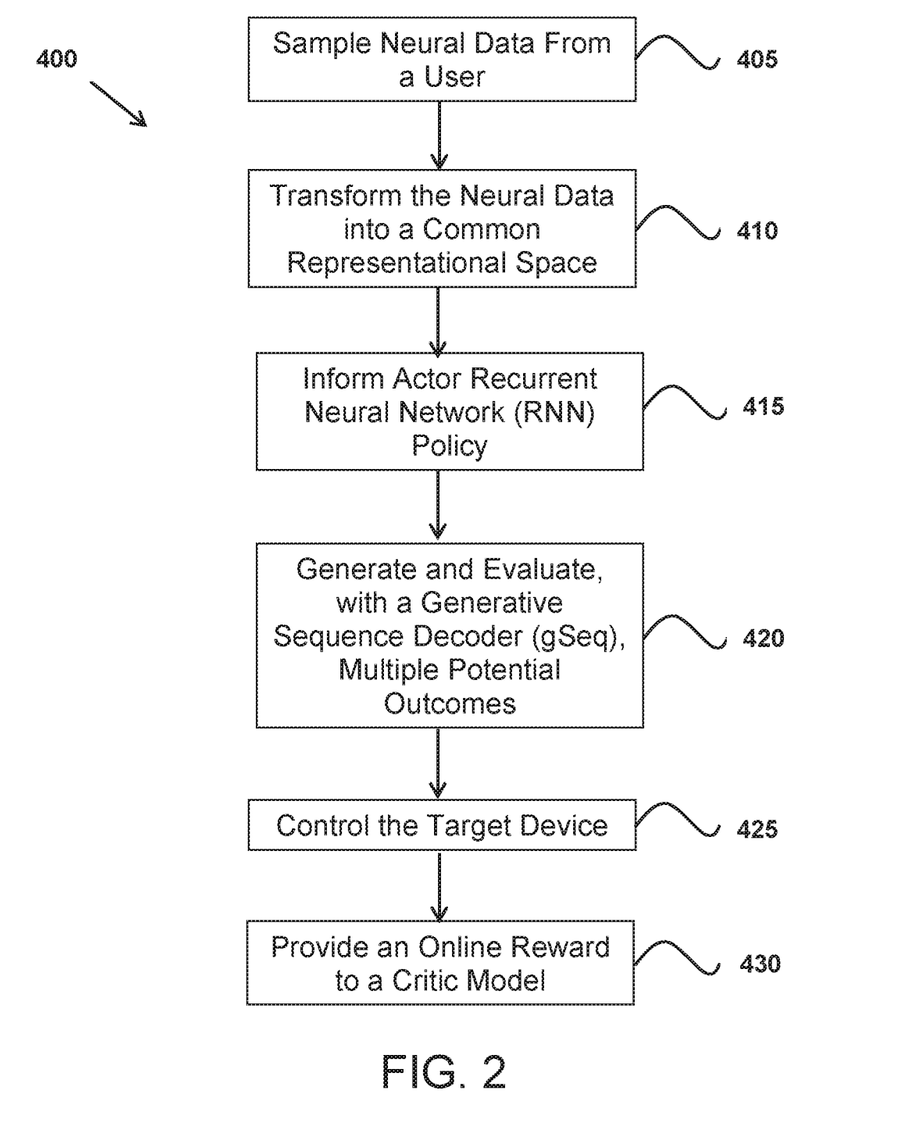
FIG. 2 is a flowchart illustrating tasks of a method for decoding neural signals into control signals for a target device according to one embodiment of the present disclosure.

FIG. 1 illustrates a brain-machine interface (BMI) system 100 according to one embodiment of the present disclosure that is configured to decode neural data 200 from users into control signals for controlling a target device (e.g., an external device) 300, such as a remote hands-free device (e.g., a robot or an unmanned aerial vehicle). FIG. 2 is a flowchart illustrating tasks of a method 400 of decoding the neural data 200 into control signals for controlling the target device 300 according to one embodiment of the present disclosure utilizing the BMI system 100 illustrated in FIG. 1.

In the illustrated embodiment, the method 400 includes a task 405 of sampling the neural data 200 from a user. The neural data 200 sampled in task 405 may be sensed invasively (e.g., from sensors surgically implanted inside the brain of the user) or non-invasively (e.g., by sensors placed outside the user's skull). In one or more embodiments, the task 405 of sampling the neural data 200 may include sampling the neural data 200 from the user while the user is performing a series of tasks with varying cognitive loads. In one or more embodiments, the task 405 of sampling the neural data 200 of the user may be performed utilizing an invasive electrocorticographic (ECoG) device or an intracranial electroencephalography (iEEG) device (e.g., Dorsal M1 and ventral sensorimotor (M1+S1) electrodes) while the user performs a finger flexion task.

In the illustrated embodiment, the method 400 also includes a task 410 of transforming the neural data 200 sampled in task 405 into a common representational space 101 (i.e., common-space neural data) stored in the BMI system 100, as shown in FIG. 1. The task 410 of transforming the neural data 200 into the common representational space 101 may be performed in any suitable manner, such as the method described in Van Uden C E, Nastase S A, Connolly A C, Feilong M, Hansen I, Gobbini M I, et al., "Modeling semantic encoding in a common neural representational space." bioRxiv. Cold Spring Harbor Laboratory; 2018:288605, the entire content of which is incorporated herein by reference. In one or more embodiments, the transformation into this common representational space 101 may be learned during initial calibration through standard optimization processes or more simply through canonical-correlation analysis. The common representational space 101 enables sharing of neural data samples from the same user across different sessions, and among different users, without sacrificing individuality (i.e., the utilization of a functionally-derived shared model space across users enables for pooling across users while maintaining the specificity of each user's model). In one or more embodiments, the task 410 of transforming the neural data 200 into the common representational space 101 includes identifying regions of the sampled neural data 200 with the most predictable or consistent activations as control signals for controlling the target device 300, and calculating subject-specific transforms to align these regions across different users. For example, in one or more embodiments, the task 410 of transforming the neural data 200 into the common representational space 101 includes calculating transformations between the neural data 200 of different users and/or the neural data 200 of the same user at different times.

In the illustrated embodiment, the method 400 also includes a task 415 of utilizing the common-space neural data 101 as a state representation to inform an Actor recurrent neural network (RNN) policy 102 of the BMI system 100 on what control signals to send to the target device 300 (e.g., an unmanned aerial vehicle or a robot arm). Task 415 may be performed utilizing a long short-term memory (LSTM) RNN architecture, such as that described in Hochreiter, S., & Schmidhuber, J. (1997). "Long short-term memory." *Neural computation*, 9(8), 1735-1780, the entire content of which is incorporated herein by reference.

In the illustrated embodiment, the method 400 also includes a task 420 of predicting, utilizing a deep RNN 103 of the BMI system 100 illustrated in FIG. 1, a control signal for the target device 300 as the mental state of the user is forming (i.e., predicting the control signal to send to the target device 300 based on the neural data in the common representational space 101 as the mental state of the user is developing). Utilizing the deep RNN 103 enables decoding multi-degree-of-freedom (multi-DOF) control signals from temporal cascades of neural activity, which provides the ability to incorporate diverse information across time and space into the control signal. The underlying learning algorithm utilized in task 420 is a generative sequence to sequence decoder capable of sequence decoding by leveraging RNN cells for the generator and discriminator components, using a tree search method on the action space, and propagating the policy reward gradient after full-sequence decoding (i.e., during the task 420 of predicting the control signals, the sequence decoder evaluates the proposed actions in a Monte-Carlo-Tree-Search like fashion). Generative sequence decoders are described in Yu L, Zhang W, Wang J, Yu Y. "SeqGAN: Sequence Generative Adversarial Nets with Policy Gradient." 2016. pp. 1-11. Available from: https://arxiv.org/abs/1609.05473, the entire content of which is incorporated herein. Monte-Carlo-Tree-Searches are described in Kocsis, L., & Szepesvári, C. (2006, September). "Bandit based monte-carlo planning." In *European conference on machine learning* (pp. 282-293). Springer, Berlin, Heidelberg, the entire content of which is incorporated herein. The implicit predictions of the tree search may be utilized to expedite control selection and thereby reduce latency for decoder classification. In this manner, the task 420 is configured to generate predictive sequences of control signals to evaluate multiple potential outcomes simultaneously. Thus, the task 420 of utilizing the deep RNN 103 is configured to improve the speed and accuracy of the BMI system 100 to control the target device 300 using the user's neural data 200.

In the illustrated embodiment, the method 400 also includes a task 425 of controlling the target device 300 (e.g., an external hands-free device such as an unmanned aerial vehicle or a robot arm) based on the neural data 200 of the user.

In the illustrated embodiment, the method 400 also includes a task 430 of providing an online reward from an online reinforcement learning agent 104 to a Critic model 105 of the BMI system 100, as illustrated in FIG. 1. In one or more embodiments, the task 430 includes extracting an intrinsic biometric-based reward signal from the user's neural data in the common representational space 101 based on the user's expectations of a successful control of the target device 300. The task 430 of extracting an intrinsic biometric-based reward signal from the user's neural data may be performed by any suitable technique, such as that described in Zhao Y, Hessburg J P, Kumar J N A, Francis J T T. "Paradigm Shift in Sensorimotor Control Research and Brain Machine Interface Control: The Influence of Context on Sensorimotor representations." bioRxiv. Cold Spring Harbor Laboratory; 2018:239814, the entire content of which is incorporated herein by reference. A suitable Critic model is described Haarnoja, T., Zhou, A., Abbeel, P., & Levine, S. (2018). "Soft actor-critic: Off-policy maximum entropy deep reinforcement learning with a stochastic actor." arXiv preprint arXiv:1801.01290, the entire content of which is incorporated herein by reference. In one or more embodiments, the task 430 includes decoding the emotional response of a user to the intended action of the target device 300. For instance, the unsuccessful translation of the neural data 200 into a control signal will result in the poor performance of the target device 300, and will thus elicit a negative emotional response from the user. Conversely, a successful translation of the neural data 200 into a control signal will result in the desired performance of the target device 300, and will thus elicit a positive emotional response from the user. In one or more embodiments, the task 430 includes transforming these positive or negative emotional response(s) into a reward signal(s) and supplying the reward signal(s) to the Critic model 105 to drive online learning (e.g., the task 430 includes extracting an intrinsic reward signal from the common representational space 101 of the neural data 200 and informing the Critic model 105 based on how successfully the intended action was performed by the target device 300). In this manner, the task 430 enables continual or substantially continual adaptation of the mapping from the neural data 200 to the output control signals for controlling the target device 300 (i.e., the online reward is configured to enable adaptation to changes in the neural data 200).

In one or more embodiments, the BMI system 100 may include the common representational space 101 of the users' neural data, the Actor RNN policy 102, the deep RNN 103, the online reinforcement learning agent 104, and the Critic model 105. In one or more embodiments, the BMI system 100 may also include the target device 300. In one or more embodiments, the target device 300 may not be part of the BMI system 100.

Reduction to Practice

Figure 3:
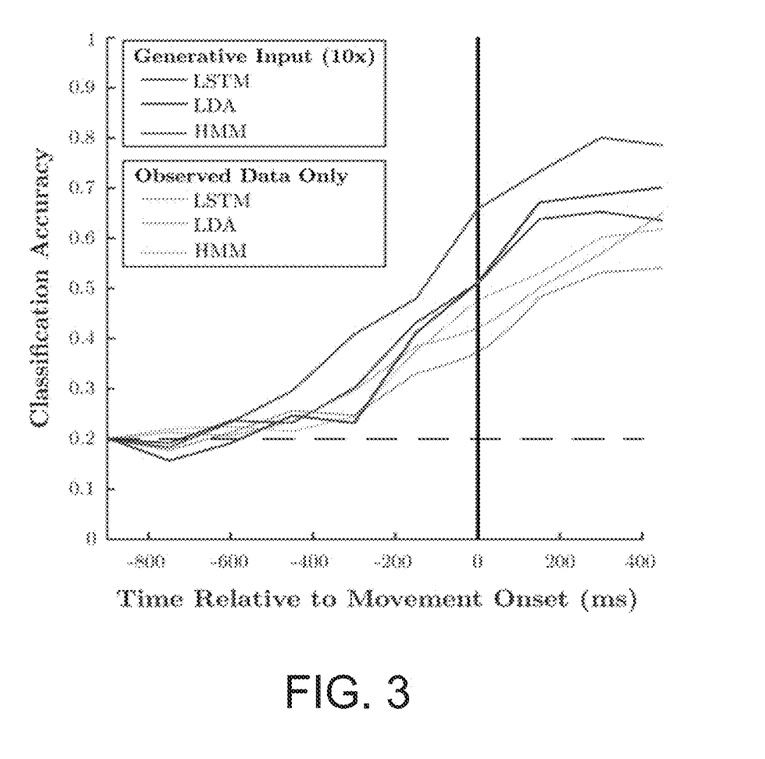
FIG. 3 is a graph comparing the performance of the systems and methods of the present disclosure to related art models (linear discriminant analysis (LDA) and hidden Markov model (HMM))

A pilot study on the efficacy of using generative inputs to increase accuracy and responsiveness of EEG decoding was performed as proof of concept of the sequence decoder network in the BMI system 100. To this end, decoder latency and performance characteristics of the generator and discriminator long short-term memory (LSTM) networks were evaluated. Invasive electrocorticographic (ECoG) recordings were utilized from a finger flexion task. High gamma power from Dorsal M1 and ventral sensorimotor (M1+S1) electrodes on a 150 millisecond (ms) window with a 50 ms slide was utilized as the representative feature. The LSTM model was initialized with a sequence autoencoder and then trained on the power-electrode features. A non-stacked LSTM was utilized with 100 hidden units and the baseline comparative models were linear discriminant analysis (LDA) such that the temporal sequence was flattened and provided as the feature and a hidden Markov model (HMM). While LDA provides a strong baseline performance for structured tasks due to it explicitly modeling the temporal response as a function of neural activity relative to movement onset, the HMM and LSTM learn a more general representation by capturing the temporal dynamics. As such, as illustrated in FIG. 3, the performance of the LSTM is shown to provide more discriminating information prior to related art LDA and HMM while also achieving better classification, especially when utilizing a generative adversarial network (GAN) without temporal relationship to augment the data to 10× the original observed data. In FIG. 3, the 10× refers to the amount of data augmentation using the generative model (i.e., 'LSTM 10×' was trained using 10× the data of 'Observed Data Only LSTM'). As shown in FIG. 3 with the dashed arrow, source data augmentation demonstrates improved sequence model (LSTM) latency compared to average of conventional models (LSTM, LDA and HMM) of approximately (about) 400 ms at 50% threshold accuracy. Accordingly, the sequence decoder of the BMI system 100 of the present disclosure exhibited improved latency and accuracy compared to related art systems and methods.

Some or all of the operations described herein (e.g., the tasks 405-430 depicted in FIG. 2) may be performed by one or more processing circuits. For example, the software components of the BMI system 100 may be hosted on a server including a processing circuit, and each user and the host may use a user interface (e.g., in a web browser) displayed by a computer including a processing circuit. The server may perform the transformation of the users' neural data into the common representational space, may apply the state representation to inform the Actor RNN policy, may apply the online reward to the Critic model, and/or may generate and evaluate potential control signals utilizing the sequence decoder, as discussed above.

Various portions of embodiments of the present invention that refer to the use of a "processing circuit" may be implemented with logic gates, or with any other embodiment of a processing unit or processing circuit. The term "processing unit" or "processing circuit" is used herein to include any combination of hardware, firmware, and software, employed to process data or digital signals. Processing unit hardware may include, for example, application specific integrated circuits (ASICs), general purpose or special purpose central processing units (CPUs), digital signal processors (DSPs), graphics processing units (GPUs), and programmable logic devices such as field programmable gate arrays (FPGAs). In a processing unit or a processing circuit, as used herein, each function is performed either by hardware configured, i.e., hard-wired, to perform that function, or by more general purpose hardware, such as a CPU, configured to execute instructions stored in a non-transitory storage medium. A processing unit or a processing circuit may be fabricated on a single printed circuit board (PCB) or distributed over several interconnected PCBs. A processing unit or a processing circuit may contain other processing units or circuits; for example a processing circuit may include two processing circuits, an FPGA and a CPU, interconnected on a PCB.

Figure 4:
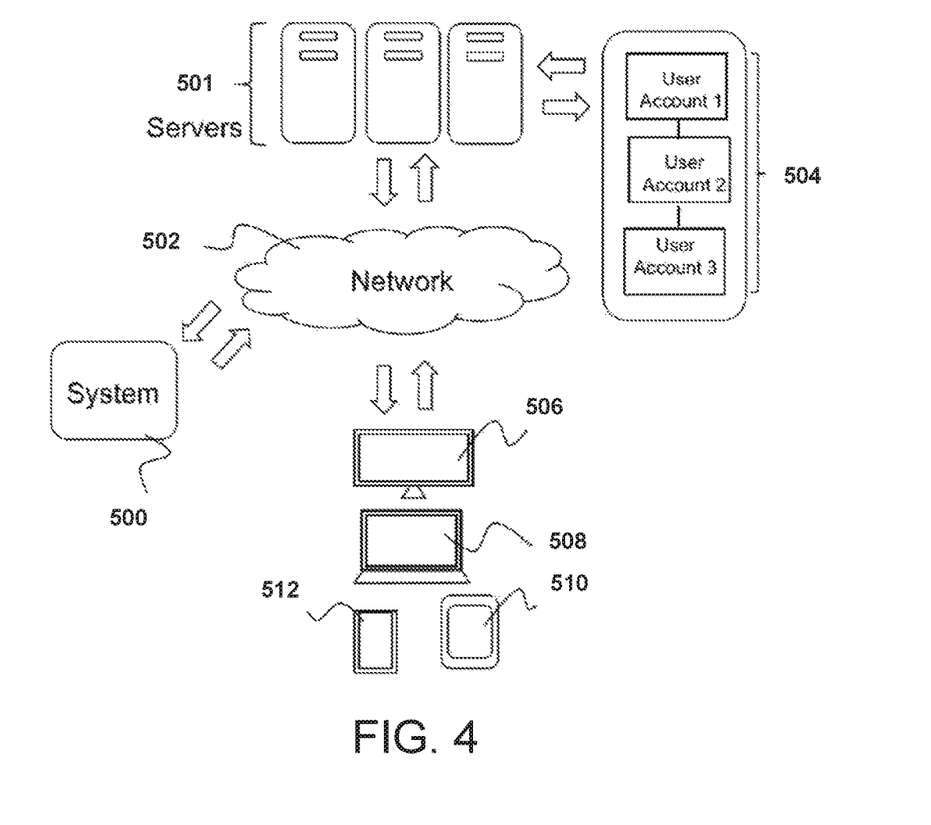
FIG. 4 is a block diagram illustrating various computerized systems communicating with one another which may be used to implement embodiments of the present invention.

FIG. 4 is a block diagram illustrating various computerized systems communicating with one another which may be used to implement embodiments of the present invention.

As shown in FIG. 4, a system 500 according to some embodiments of the present disclosure connects with servers 501 (e.g., device to be operated) to perform the operations described herein, such as transforming the users' neural data into the common representational space, applying the state representation to inform the Actor RNN policy, applying the online reward to the Critic model, and/or generating and evaluating potential control signals utilizing the sequence decoder.

The system 500 connects via a network 502 to the servers 501 to send and/or receive information relating to the neural data and/or control signal derived therefrom of various user accounts (element 504) that may be accessed via mobile and non-mobile devices, non-limiting examples of which include desktop computers 506, laptop computers 508, smartphones 510, and other mobile devices 512. As can be appreciated by one skilled in the art, the user device is any device that can receive and transmit data (e.g., the neural data) via the network 502.

Figure 5:
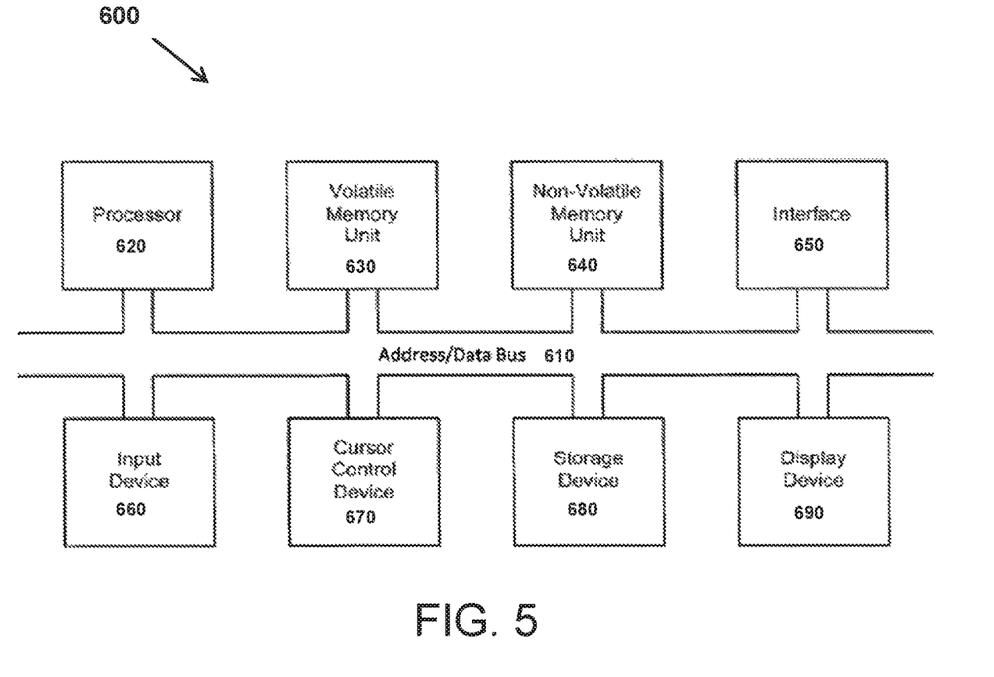
FIG. 5 is a block diagram illustrating a processing system, a processing circuit, or a portion of a processing system or processing circuit used in conjunction with at least one embodiment of the present invention.

FIG. 5 is a block diagram illustrating a processing system, a processing circuit, or a portion of a processing system or processing circuit, referred to herein as a computer system, used in conjunction with at least one embodiment of the present invention.

An exemplary computer system 600 in accordance with an embodiment is shown in FIG. 5. Exemplary computer system 600 is configured to perform calculations, processes, operations, and/or functions associated with a program or algorithm. In one embodiment, certain processes and steps discussed herein are realized as a series of instructions (e.g., software program) that reside within computer readable memory units and are executed by one or more processing circuits of exemplary computer system 600. When executed, the instructions cause exemplary computer system 600 to perform specific actions and exhibit specific behavior, such as described herein.

Exemplary computer system 600 may include an address/data bus 610 that is configured to communicate information. Additionally, one or more data processing units, such as processing circuit 620, are coupled with address/data bus 610. Processing circuit 620 is configured to process information and instructions. In an embodiment, processing circuit 620 is a microprocessor. Alternatively, processing circuit 620 may be a different type of processor such as a parallel processor, or a field programmable gate array.

Exemplary computer system 600 is configured to utilize one or more data storage units. Exemplary computer system 600 may include a volatile memory unit 630 (e.g., random access memory ("RAM"), static RAM, dynamic RAM, etc.) coupled with address/data bus 610, wherein volatile memory unit 630 is configured to store information and instructions for processing circuit 620. Exemplary computer system 600 further may include a non-volatile memory unit 640 (e.g., read-only memory ("ROM"), programmable ROM ("PROM"), erasable programmable ROM ("EPROM"), electrically erasable programmable ROM "EEPROM"), flash memory, etc.) coupled with address/data bus 610, wherein non-volatile memory unit 640 is configured to store static information and instructions for processing circuit 620. Alternatively exemplary computer system 600 may execute instructions retrieved from an online data storage unit such as in "Cloud" computing. In an embodiment, exemplary computer system 600 also may include one or more interfaces, such as interface 650, coupled with address/ data bus 610. The one or more interfaces are configured to enable exemplary computer system 600 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one embodiment, exemplar computer system 600 may include an input device 660 coupled with address/data bus 610, wherein input device 660 is configured to communicate information (e.g., neural data) to processing circuit 620. In accordance with one embodiment, input device 660 is one or more non-invasive sensors (e.g., sensors placed outside the user's skull) or invasive sensors (e.g., sensors surgically implanted inside the brain), such as an invasive electrocorticographic (ECoG) device or an intracranial electroencephalography (iEEG) device (e.g., Dorsal M1 and ventral sensorimotor (M1+S1) electrodes). Alternatively, input device 660 may be an alphanumeric input device, such as a keyboard, that may include alphanumeric and/or function keys. In an embodiment, exemplar computer system 600 may include a cursor control device 670 coupled with address/data bus 610, wherein cursor control device 670 is configured to communicate user input information and/or command selections to processing circuit 620. In an embodiment, cursor control device 670 is implemented using a device such as a mouse, a track-ball, a track-pad, an optical tracking device, or a touch screen. The foregoing notwithstanding, in an embodiment, cursor control device 670 is directed and/or activated via input from input device 660, such as in response to the use of special keys and key sequence commands associated with input device 660. In an alternative embodiment, cursor control device 670 is configured to be directed or guided by voice commands.

In an embodiment, exemplary computer system 600 further may include one or more optional computer usable data storage devices, such as storage device 680, coupled with address/data bus 610. Storage device 680 is configured to store information and/or computer executable instructions. In one embodiment, storage device 680 is a storage device such as a magnetic or optical disk drive (e.g., hard disk drive ("HDD"), floppy diskette, compact disk read only memory ("CD-ROM"), digital versatile disk ("DVD")). Pursuant to one embodiment, a display device 690 is coupled with address/data bus 610, wherein display device 690 is configured to display video and/or graphics. In an embodiment, display device 690 may include a cathode ray tube ("CRT"), liquid crystal display ("LCD"), field emission display ("FED"), plasma display or any other display device suitable for displaying video and/or graphic images and alphanumeric characters recognizable to a user.

Exemplary computer system 600 is presented herein as an exemplary computing environment in accordance with an embodiment. However, exemplary computer system 600 is not strictly limited to being a computer system. For example, an embodiment provides that exemplary computer system 600 represents a type of data processing analysis that may be used in accordance with various embodiments described herein. Moreover, other computing systems may also be implemented. Indeed, the spirit and scope of the present technology is not limited to any single data processing environment. Thus, in an embodiment, one or more operations of various embodiments of the present technology are controlled or implemented using computer-executable instructions, such as program modules, being executed by a computer. In one exemplary implementation, such program modules include routines, programs, objects, components and/or data structures that are configured to perform particular tasks or implement particular abstract data types. In addition, an embodiment provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

It should be understood that the drawings are not necessarily to scale and that any one or more features of an embodiment may be incorporated in addition to or in lieu of any one or more features in another embodiment, and the orientation of the components may have any other suitable orientation in addition to the orientation depicted in the figures. Moreover, the tasks described above may be performed in the order described or in any other suitable sequence. Additionally, the methods described above are not limited to the tasks described. Instead, for each embodiment, one or more of the tasks described above may be absent and/or additional tasks may be performed. As used herein, the term "substantially," "about," "approximately," and similar terms are used as terms of approximation and not as terms of degree, and are intended to account for the inherent deviations in measured or calculated values that would be recognized by those of ordinary skill in the art.

While this invention has been described in detail with particular references to exemplary embodiments thereof, the exemplary embodiments described herein are not intended to be exhaustive or to limit the scope of the invention to the exact forms disclosed. Persons skilled in the art and technology to which this invention pertains will appreciate that alterations and changes in the described structures and methods of assembly and operation can be practiced without meaningfully departing from the principles, spirit, and scope of this invention, as set forth in the following claims, and equivalents thereof.

What is claimed is:

1. A brain-machine interface system configured to decode neural signals to control a target device, the brain-machine interface system comprising:
   at least one sensor configured to sample the neural signals; and
   a computer-readable storage medium having software instructions stored therein, which, when executed by a processor, cause the processor to:
      transform the neural signals into a common representational space stored in the brain-machine interface system;
      provide the common representational space as a state representation to inform an Actor recurrent neural network policy of the brain-machine interface system;
      generate and evaluate, utilizing a deep recurrent neural network of the brain-machine interface system having a generative sequence decoder, predictive sequences of control signals for the target device;
      supply a specific control signal derived from the predictive sequences of control signals to the target device to achieve an output of the target device;
      determine an intrinsic biometric-based reward signal, from the common representational space, based on an expectation of the output of the target device; and
      supply the intrinsic biometric-based reward signal to a Critic model of the brain-machine interface system.

2. The brain-machine interface system of claim 1, wherein the at least one sensor is configured to sample the neural signals invasively or non-invasively.

3. The brain-machine interface system of claim 2, wherein a sensor of the at least one sensor comprises an invasive electrocorticographic (ECoG) device or an intracranial electroencephalography (iEEG) device.

4. The brain-machine interface system of claim 1, wherein transforming the neural signals into the common representational space comprises:
   identifying regions of the neural signals with informative activations for controlling the target device, and
   performing subject-specific transforms to align the regions across different users.

5. The brain-machine interface system of claim 1, wherein the intrinsic biometric-based reward signal is indicative of a positive emotional response when the output of the target device matches a user's intended output.

6. The brain-machine interface system of claim 1, wherein the intrinsic biometric-based reward signal is indicative of a negative emotional response when the output of the target device does not match a user's intended output.

7. The brain-machine interface system of claim 1, wherein the software instructions, when executed by the processor, cause the processor to generate and evaluate the predictive sequences of the control signals utilizing a tree search.

8. A non-transitory computer-readable storage medium having software instructions stored therein, which, when executed by a processor, cause the processor to:
   transform neural data from an individual user into a common representational space and store the common representation space in a memory device of a brain-machine interface system;
   provide the common representational space as a state representation to inform an Actor recurrent neural network policy of the brain-machine interface system;
   generate and evaluate, utilizing a deep recurrent neural network of the brain-machine interface system having a generative sequence decoder, predictive sequences of control signals for a target device;
   supply a specific control signal derived from the predictive sequences of control signals to the target device to produce an output of the target device;
   determine an intrinsic biometric-based reward, from the common representational space, based on the individual user's expectation of the output of the target device; and
   supply the intrinsic biometric-based reward to a Critic model of the brain-machine interface system.

9. The non-transitory computer-readable storage medium of claim 8, wherein the instructions, when executed by the processor, cause the processor to transform the neural data into the common representational space by:
   identifying regions of the neural data with informative activations for controlling the target device, and
   performing subject-specific transforms to align the regions across different users.

10. The non-transitory computer-readable storage medium of claim 8, wherein the instructions, when executed by the processor, cause the processor to determine the intrinsic biometric-based reward by decoding an emotional response from the individual user to the output of the target device.

11. The non-transitory computer-readable storage medium of claim 10, wherein the intrinsic biometric-based reward is a positive emotional response when the output of the target device matches the individual user's intended output.

12. The non-transitory computer-readable storage medium of claim 10, wherein the intrinsic biometric-based reward is a negative emotional response when the output of the target device does not match the individual user's intended output.

13. The non-transitory computer-readable storage medium of claim 8, wherein the software instructions, when executed by the processor, cause the processor to generate and evaluate the predictive sequences of the control signals utilizing a tree search.

14. A method of controlling a target device utilizing neural data, the method comprising:
   sampling, with at least one sensor, the neural data from a user;
   transforming, with a processor of a brain-machine interface system, the neural data into a common representational space and storing the common representational space in a memory device of the of a brain-machine interface system;
   supplying, by the processor of the brain-machine interface system, the common representational space as a state representation to inform an Actor recurrent neural network policy of the brain-machine interface system;
   generating and evaluating, utilizing a deep recurrent neural network of the brain-machine interface system having a generative sequence decoder, predictive sequences of control signals for the target device;
   supplying, by the processor of the brain-machine interface system, a specific control signal derived from the predictive sequences of control signals to the target device to produce an output of the target device;
   determining, by the processor of the brain-machine interface system, an intrinsic reward, from the common representational space, based on the user's expectation of the output of the target device; and
   supplying, by the processor of the brain-machine interface system, the intrinsic reward to a Critic model of the brain-machine interface system.

15. The method of claim 14, wherein the evaluating the predictive sequences of the control signals comprises a tree search.

16. The method of claim 14, wherein the transforming the neural data into the common representational space comprises:
   identifying regions of the neural data with informative activations for controlling the target device, and
   performing subject-specific transforms to align the regions across different users.

17. The method of claim 14, wherein the determining the intrinsic reward comprises decoding an emotional response from the user to the output of the target device.

18. The method of claim 17, wherein the emotional response is a positive emotional response when the output of the target device is expected.

19. The method of claim 17, wherein the emotional response is a negative emotional response when the output of the target device is unexpected.

20. The method of claim 14, wherein the sampling the neural data from the user is performed invasively or non-invasively.

* * * * *